United States Patent [19]

Becker et al.

[11] Patent Number: 4,469,483
[45] Date of Patent: Sep. 4, 1984

[54] RADIOPAQUE CATHETER

[75] Inventors: Lawrence F. Becker, Chicago; Christine Pham, Wheeling, both of Ill.

[73] Assignee: Baxter Travenol Laboratories, Inc., Deerfield, Ill.

[21] Appl. No.: 411,177

[22] Filed: Aug. 25, 1982

[51] Int. Cl.³ ............................................. A61M 25/00
[52] U.S. Cl. ............................ 604/280; 128/DIG. 21
[58] Field of Search ...................... 138/118; 604/280; 128/DIG. 21

[56] References Cited

U.S. PATENT DOCUMENTS

| | | | |
|---|---|---|---|
| Re. 25,788 | 6/1965 | Sheridan | 128/348 |
| 2,212,334 | 8/1940 | Wallerich | 18/38 |
| 2,227,682 | 1/1941 | Wade | 18/57 |
| 2,233,987 | 3/1941 | Orsini | 18/12 |
| 2,237,218 | 4/1941 | Flynn | 128/349 |
| 2,237,219 | 4/1941 | Flynn | 128/349 |
| 2,237,220 | 4/1941 | Flynn | 128/349 |
| 2,857,915 | 10/1958 | Sheridan | 128/349 |
| 2,930,377 | 3/1960 | Cowley | 128/344 |
| 3,056,428 | 10/1962 | Brown et al. | 138/118 |
| 3,070,132 | 12/1962 | Sheridan | 138/118 |
| 3,097,058 | 7/1963 | Branscum et al. | 18/55 |
| 3,190,290 | 6/1965 | Alley et al. | 128/348 |
| 3,228,894 | 1/1966 | Jeckel et al. | 128/348 |
| 3,314,430 | 4/1967 | Alley et al. | 128/350 |
| 3,529,633 | 9/1970 | Vaillancourt et al. | 264/173 |
| 3,599,641 | 8/1971 | Sheridan | 128/348 |
| 3,608,555 | 9/1971 | Greyson | 128/348 |
| 3,618,614 | 11/1971 | Flynn | 128/348 |
| 3,749,134 | 7/1973 | Slingluff | 138/177 |
| 3,766,916 | 10/1973 | Moorehead et al. | 128/214.4 |
| 3,861,396 | 1/1975 | Vaillancourt et al. | 128/350 R |
| 3,914,002 | 10/1975 | Berliner et al. | 339/16 R |
| 4,027,659 | 6/1977 | Slingluff | 128/2 M |
| 4,105,732 | 8/1978 | Slingluff | 264/173 |
| 4,196,731 | 4/1980 | Laurin et al. | 604/280 |
| 4,277,432 | 7/1981 | Woinowski | 264/173 |

Primary Examiner—C. Fred Rosenbaum
Assistant Examiner—Michelle N. Lester
Attorney, Agent, or Firm—Garrettson Ellis; Paul C. Flattery

[57] ABSTRACT

A silicone rubber catheter carries radiopaque stripes comprising a mixture of silicone rubber and the finely divided radiopaque material, the stripes being spaced from each other by transparent, longitudinal segments. The radiopaque stripes are preferably positioned in diametrically opposed, spaced relation to each other about the circumference of the catheter and occupy a total of 50° to 270° of the catheter circumference. The elongation of the catheter portion defining the stripes is preferably at least as great as the elongation of the catheter portion defining the transparent, longitudinal segments, and the tensile and tear strengths of the transparent segments are preferably higher, so that upon stretching of the catheter most of the stress can be diverted to the transparent segments of the catheter.

9 Claims, 3 Drawing Figures

RADIOPAQUE CATHETER

TECHNICAL FIELD AND PRIOR ART

The invention disclosed herein relates to radiopaque silicone rubber materials and catheter designs utilizing radiopaque materials.

Catheters with radiopaque stripes are known. For example, see Vaillancourt U.S. Pat. No. 3,529,633, or the FLASH-CATH® intravascular catheter sold by Travenol Laboratories, Inc. of Deerfield, Illinois is a catheter made of polytetrafluoroethylene having an outer diameter of about 1 mm., and three spaced, longitudinal, radiopaque stripes made of barium sulfate. The radiopaque stripes are generally encapsulated by the polytetrafluoroethylene of the catheter, being basically solid lines of finely divided barium sulfate surrounded by the plastic material.

Silicone catheter tubing containing about 33 percent by weight of barium sulfate in a stripe is also known, being available, for example, from Dow Corning.

A problem which often exists, particularly in small catheters of typically no more than 4 mm. outer diameter and often having inner diameters of 2 mm. or less, is that it is difficult to provide enough radiopaque material to the catheter to provide really good visibility of the catheter on x-ray film. The small size of the catheter severely limits the mass of radiopaque material which can be present. One serious problem that has limited the amount of radiopaque material that can be present in a catheter is the fact that if a radiopaque material such as barium sulfate is dispersed into the plastic catheter material, its physical properties such as ultimate tensile strength can be severely deteriorated. Thus the catheter can become unduly weak.

On the other hand, it is desirable for the interior of the catheter to be visible, so the catheter should have transparent sections.

Accordingly, it has been previously deemed unfeasible to load a silicone catheter with as much as 50 percent by weight of barium sulfate as a radiopaque material, for example, because of the deterioration of physical properties that can result from such heavy loadings. However, lighter loadings of barium sulfate in a small catheter made of silicone rubber, for example, can result in difficulties of visibility of the catheter on x-ray film.

In accordance with this invention, a particular arrangement of radiopaque stripes is provided which exhibits improved x-ray visibility in all positions of the catheter. Also, the catheter may be formulated in accordance with this invention in a manner that permits the radiopaque stripes to carry increased amounts of radiopaque agents such as barium sulfate, with less diminution of the tensile strength of the overall catheter as it is fabricated, so that the radiopaque stripe portions of the catheter can carry higher loadings of radiopaque agent, for improved x-ray visibility.

DESCRIPTION OF INVENTION

In accordance with one aspect of this invention, a catheter made of silicone rubber or the like carries a pair of longitudinal stripes of radiopaque material, the stripes being positioned in diametrically opposed, spaced relation to each other about the circumference of the catheter and comprising a mixture of silicone rubber and the finely divided radiopaque material. The catheter also defines a pair of diametrically opposed, transparent, longitudinal segments positioned between the stripes for viewing the catheter interior. Typically the stripes containing radiopaque material occupy a total of 50° to 270° of the catheter circumference, and preferably 90° to 180°.

Because of the use of stripes of substantial width (typically at least 45° and preferably about 60° to 100°) and their diametric positioning, increased x-ray visibility is provided by the fact that from whatever position the catheter occupies the stripes are either seen from a substantially edge-on view, or seen in overlapping relationship. Thus x-rays passing laterally through the catheter will tend to either pass through both of the stripes in their diametrically opposed relation, or the x-rays will pass sideways throught the stripes. In either event the x-rays pass through an increased amount of radiopaque agent, and thus the radiopaque stripes tend to be more visible on opposed x-ray film than stripes of radiopaque agent positioned in a different configuration.

Also, since the transparent, longitudinal segments are in opposed relation to each other, one can see through the catheter for easy viewing of the interior.

The invention of this application finds particular use in smaller catheters, where the catheter may have an inner diameter of no more than 2 mm and an outer diameter of no more than 4 mm. Furthermore, the radiopaque stripes may preferably comprise a first silicone rubber and barium sulfate mixture containing from 35 or 40 to 70 weight percent of barium sulfate and preferably about 50 weight percent of barium sulfate. This first silicone rubber, when free of barium sulfate and cured, may preferably have an elongation of 900% to 1,100% and an ultimate tensile strength of at least 1,100 p.s.i. When barium sulfate is added, these values are reduced.

The transparent longitudinal segments of the catheter of this invention may comprise a second, cured silicone rubber having an elongation of less than the first silicone rubber when free of barium sulfate, typically 350% to 600%, and an ultimate tensile strength of at least 900 p.s.i.

Preferably, in accordance with this invention, the elongation of the catheter portion which defines the radiopaque stripes is formulated to be essentially at least as great as the elongation of the catheter portion defining the transparent, longitudinal segments, and the ultimate tensile and tear strengths of the catheter portion defining the transparent, longitudinal segments is greater than the ultimate tensile and tear strengths of the catheter portion defining the radiopaque stripes.

Accordingly, as the catheter is stretched, most of the stress is diverted to the transparent, longitudinal segments because of its typically lower elongation, and its higher modulus and tensile strength, which tends to protect the stripe-defining catheter portions from excessive stress. Because of this arrangement, higher loadings of radiopaque agents such as barium sulfate can be provided to the stripe portions without resulting in a catheter which is impractically weak in its overall tensile strength, while at the same time the higher radiopaque loading provides greater x-ray visibility to the catheter.

The term "elongation" as used herein is the percentage that the material specified can stretch without breaking and may be tested in accordance with ASTM D412.

The term "ultimate tensile strength" or "tensile strength" means that amount of stretching force that is required to break the material and may be measured by ASTM D412.

The term "tear strength" is as defined by ASTM D624.

Other radiopaque fillers such as tungsten, tungsten dioxide, tungsten trioxide, stainless steel powder, silver iodide, or iodinated organic compounds may also be used in this invention.

While the catheter of this invention preferably has diametrically opposed longitudinal stripes of radiopaque material, it is possible that other stripe configurations may also be used in this invention, in which the clear material of the catheter has a higher tensile strength, a higher tear strength, and typically a lower elongation than the stripe material.

BRIEF DESCRIPTION OF DRAWINGS

Referring to the drawings.

DESCRIPTION OF SPECIFIC EMBODIMENT

Figure 1:
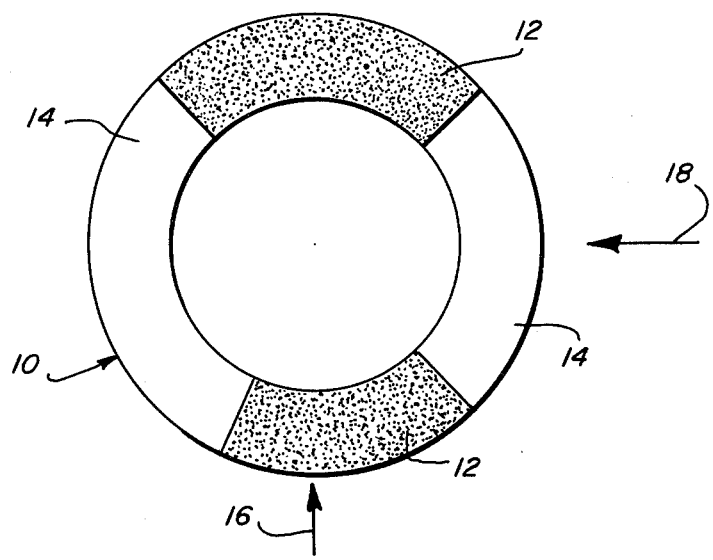
FIG. 1 is a transverse sectional view, greatly enlarged, of catheter tubing in accordance with this invention.

Referring to FIG. 1, coextruded silicone catheter tubing 10 is shown in section, being part of any desired catheter design or the like and preferably being an intravascular catheter of small size, for example, an outer diameter of 0.055 to 0.08 inch and an inner diameter of 0.03 to 0.05 inch. Specifically, the tubing may have an outer diameter of 0.061 inch and an inner diameter of 0.036 inch plus or minus 0.002–0.003 inch. Alternatively, the catheter tubing may have an outer diameter of 0.069 inch and an inner diameter of 0.040 inch plus or minus 0.002–0.003 inch.

As seen, catheter 10 defines a pair of longitudinal stripes 12 which contain a radiopaque material such as barium sulfate intimately mixed with the silicone formulation. Stripes 12 are positioned in diametrically opposed, spaced relation to each other about the circumference of catheter 10. Catheter 10 also defines a pair of diametrically opposed, transparent longitudinal segments 14 which are positioned between stripes 12. Accordingly, while the catheter is visible to x-rays by radiopaque stripes 12, the contents and interior of the catheter can also be viewed through clear segments 14. The viewing is rendered easy since the catheter can be held up to a light in back of it, and the light passes through both opposed clear sections 14.

It can also be seen that catheter 10 exhibits improved radiopaque characteristics from any direction of view. For example, from direction 16, as shown by the arrow, x-rays passing through a certain portion of the catheter must pass through both of the opaque stripes 12, and thus the presence of opaque stripes 12 is more clearly recorded on x-ray film. Similarly, from direction 18, x-rays passing through lateral portions of the catheter must pass through a substantially increased thickness of each of lines 12, and thus a thin, double-lined indication of the presence of catheter 10 shows up more readily on x-ray film if the direction of exposure is in this direction.

An added reason for the improved x-ray visibility of the catheter of this invention is that stripes 12 may contain higher loadings of radiopaque agent such as barium sulfate. The specific formulation of the material of stripes 12 may be equal parts by weight of finely powdered barium sulfate with a silicone rubber formulation sold by Rhone-Poulenc Inc. under the trademark Rhodia RS-1903; 0.4936 weight fraction of each of that silicone formulation and barium sulfate being mixed along with 0.0128 weight fraction of Rhone-Poulenc curing catalyst DBP-50 with intensive mixing (using, for example, a Banbury intensive batch mixer), to form a generally homogeneous silicone elastomer stock which can be extruded with the clear silicone elastomer stock to form catheter 10.

The clear silicone elastomer stock that is used to make longitudinal segments 14 may comprise 0.9872 weight fraction of Rhone-Poulenc silicone formulation sold as Rhodia RS1907, and 0.0128 weight fraction of Rhone-Poulenc DBP-50 curing catalyst.

As reported by a data sheet of Rhone-Poulenc, RS1903 exhibits a tensile strength of 1150 and a percent elongation of 1000. RS1907 exhibits a tensile strength of 1150 and a percent elongation of 500. Both formulations are also relatively high tear elastomer formulations after cure, with the latter silicone formulation having a higher Shore "A" hardness after cure.

Samples of the barium sulfate filled formulation of which the stripe portions 12 of the catheter are made had a percent elongation of an average of about 407 percent (ranging between 310 and 470 percent) and an ultimate tensile strength of an average of 474 pounds per square inch (ranging between 360 and 545 pounds per square inch), when testing strips of the material having an average thickness of 0.085 inch and a width of 0.228 inch. Different sample pieces exhibited an average tear strength of 72 lb/in.

Samples of the clear silicone elastomer stock, as formulated for use in making the transparent longitudinal segments 14 of this invention, were found by testing to have a percent elongation of an average of 397 (ranging from 360 to 430) and a tensile strength of an average of 974 pounds per square inch (ranging from 947 to 1004) when testing cured strips of the material having an average thickness of 0.081 inch and a width of 0.228 inch. Also the clear silicone elastomer stock had much higher tear strength, an average of 181 lb/in.

It can be seen that the silicone formulation of stripes 12, prior to addition of the barium sulfate, has a substantially higher elongation than the silicone formulation of segments 14. As a result, upon addition of the barium sulfate, the striped sections 12 can continue to have equal or higher elongation than sections 14, while sections 14 have the greater tensile and tear strengths, so that upon stretching of the cured catheter most of the stress is carried by sections 14, thus protecting stripes 12 from rupturing, and permitting higher loadings of barium sulfate to provide greater x-ray visibility.

Catheter 10 may be coextruded by known and conventional means into the form disclosed herein from the two silicone elastomer stocks described above. The respective angular widths of sections 12 as shown are specifically shown to be 67° and 98°, while the transparent segments in this specific embodiment exhibit respective angular widths of 89° and 115°. However, it is understood that variations of these angles will be customary.

The resulting catheter tubing 10 may have an outer diameter of 0.069 inch (±0.03) and an inner diameter of 0.040 inch (±0.002). A specific catheter tubing 10, made as described above, exhibited a breaking force of 2.47 pounds, a tensile strength of 994 pounds per square inch, an elongation of 469 percent, a force at 100 percent elongation of 0.8 pounds, a 100 percent modulus of 322 pounds per square inch, and a Shore A durometer of 65–70. Catheter tubing 10 exhibited superior visibility on x-ray film taken in any lateral direction. From direction 18 a double line configuration is noted, while from direction 16 a single broad line can be readily seen.

Figure 3:
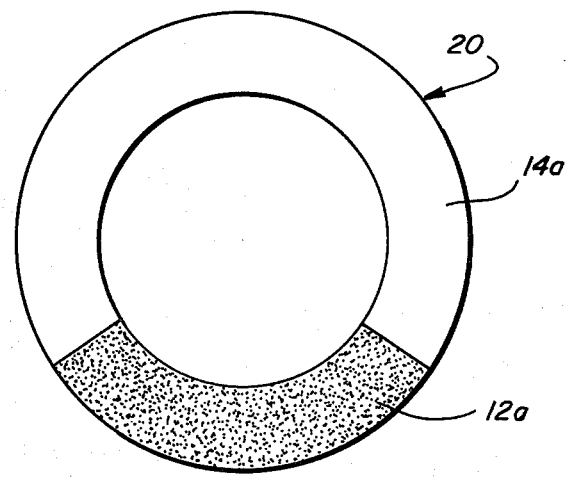
FIG. 3 is a transverse sectional view, greatly enlarged of another design of catheter tubing in accordance with this invention.

Referring to FIG. 3, catheter tubing 20 may be similar to catheter tubing 10 both in dimension and in the formulations used to fabricate stripe 12a and transparent longitudinal segment 14a. As can be seen, only one longitudinal stripe 12a is used in this embodiment, with variable angular width specifically shown to be about 120°. The remainder of the catheter constitutes clear segment 14a which is shown to have an angular width on the order of 240°. Catheter tubing 20 may be coextruded as in accordance with the previous embodiment, and equal or lesser elongation, and higher tensile and tear strengths of clear segment 14a, as previously, protects stripe 12a from rupture under normal circumstances of use.

Figure 2:
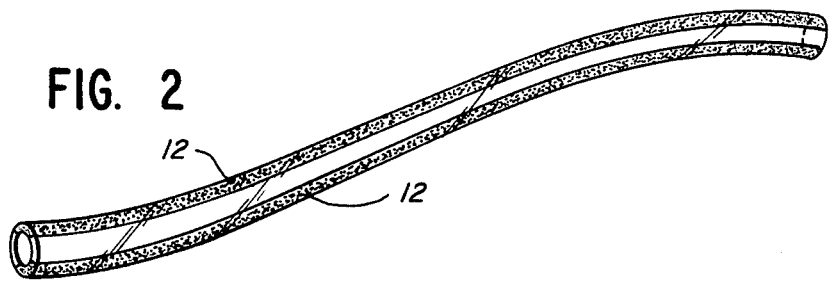
FIG. 2 is a perspective view of the tubing of FIG. 1.

Both of the embodiments disclosed in this invention provide superior visibility on x-ray film due to their higher loading of barium sulfate or other radiopaque agent, and, in the case of the embodiment of FIGS. 1 and 2, due to the geometric arrangement of the pair of opposed, longitudinal, radiopaque stripes. Also the contents of the catheter are readily visible despite the improved radiopaque characteristic.

The above has been offered for illustrative purposes and is not intended to limit the scope of the invention of this application, which is as defined in the claims below.

That which is claimed is:

1. A catheter comprising a plastic tubular member, said member including longitudinal stripe means comprising radiopaque material mixed with the plastic of the tubular member, and longitudinal segment means of transparent material positioned beside said stripe means, the material of said stripe means having at least equal elongation and less ultimate tensile strength than the material of said transparent segment means.

2. The catheter of claim 1 in which said longitudinal stripe means comprises a pair of opposed, spaced radiopaque stripes, and said segment means defines a pair of opposed, transparent, longitudinal segments positioned between the stripes for viewing the interior of the tubular member.

3. The catheter of claim 1 in which the material of said stripe means has greater elongation than the material of the transparent segment means.

4. The catheter of claim 1 in which said stripe means occupies from 50° to 270° of the circumference of the tubular member.

5. The catheter of claim 4 in which said plastic comprises silicone rubber, said stripe means containing from 35 to 70 weight percent of barium sulfate mixed with the silicone rubber.

6. A catheter comprising a silicone rubber tubular member, said member including a pair of longitudinal stripes of radiopaque material, said stripes being positioned in diametrically opposed, spaced relation to each other about the circumference of the tubular member and comprising a mixture of silicone rubber and finely divided barium sulfate containing from 35 to 70 weight percent of barium sulfate, said tubular member also defining a pair of diametrically opposed, transparent, longitudinal segments positioned between said stripes for viewing the catheter interior of the tubular member, said stripes occupying a total of 50° to 270° of the circumference of the tubular member, said tubular member having an inner diameter of no more than 2 mm. and an outer diameter of no more than 4 mm., the elongation of the tubular member portion defining said stripes being at least equal to the elongation of the tubular member portion defining said transparent, longitudinal segments, and the ultimate tensile strength and tear strength of the tubular member portion defining the transparent, longitudinal segments is greater than the ultimate tensile strength and tear strength of the tubular member portion defining the radiopaque stripes.

7. The catheter of claim 6 in which the catheter portion defining said stripes has greater elongation than the catheter portion defining the transparent longitudinal segments.

8. The catheter of claim 6 in which said stripes comprise a first silicone rubber which, when free of barium sulfate and cured, has an elongation of 900% to 1,100% and an ultimate tensile strength of at least 1,100 p.s.i.

9. The catheter of claim 8 in which said transparent longitudinal segments comprise a second silicone rubber having an elongation of 350% to 600% and an ultimate tensile strength of at least 900 p.s.i.

* * * * *